United States Patent [19]
Lynch et al.

[11] Patent Number: 5,209,853
[45] Date of Patent: May 11, 1993

[54] LIQUID CHROMATOGRAPHY

[75] Inventors: Roderick J. Lynch, Ely; Gregory J. Measures; Charles V. Perkins, both of Cambridge, all of United Kingdom

[73] Assignee: U.S. Philips Corporation, New York, N.Y.

[21] Appl. No.: 865,737

[22] Filed: Apr. 9, 1992

Related U.S. Application Data

[63] Continuation of Ser. No. 513,351, Apr. 19, 1990, abandoned.

[30] Foreign Application Priority Data

Apr. 20, 1989 [GB] United Kingdom ............... 8908934

[51] Int. Cl.$^5$ .............................................. B01D 15/08
[52] U.S. Cl. ................................... 210/656; 210/198.2
[58] Field of Search .................... 210/656, 659, 96.1, 210/101, 198.2; 422/70; 436/161

[56] References Cited

U.S. PATENT DOCUMENTS

| | | | |
|---|---|---|---|
| 4,579,663 | 4/1986 | Poile | 210/656 |
| 4,719,017 | 1/1988 | Uchino | 210/656 |
| 4,969,993 | 11/1990 | Nash | 210/143 |

OTHER PUBLICATIONS

Berridge, "Using a Microprocessor in High Performance Liquid Chromatography", Microprocessors and Microsystems 7(1) Jan. 1983, pp. 19-23.

Haleem Issaq, "Computer-Assisted HPLC", American Laboratory, Feb. 1983, pp. 41-46.

Naisch, "Evaluation of a Complete HPLC Solvent Optimization System Involving Piece-Wise Quadratic Modelling", Chromatographia, vol. 29, No. 1/2, Jan. 1990, pp. 79-89.

Schoenmakers, "Criteria for Judging the Quality of Separation in Chromatograms Containing Solvent Peaks" Chromatographia 24 (1987) pp. 579-587.

Schoenmakers, "Correction of the Resolution Function for Non-Ideal Peaks", Journal of Chromatography 458 (1988) pp. 355-370.

Schoenmakers, "Criteria for Comparing the Quality of Chromatographs with Great Variations in Capacity Factors", Journal of Liquid Chromatography, 10(8 and 9), 1865-1886 (1987).

Vandeginste, "Multicomponent Self-Modelling Curve Resolution in High-Performance Liquid Chromatography by Iterative Target Transformation Analysis", Analytica Chimica Acta, 173 (1985) pp. 253-264.

Primary Examiner—Ernest G. Therkorn
Attorney, Agent, or Firm—Norman N. Spain

[57] ABSTRACT

A method of analysis by liquid chromatography and liquid chromatograph apparatus are disclosed. The method and apparatus are arranged to enable a chromatographer to locate an optimum solvent composition for a particular analysis. A display is produced which shows simltaneously a contour map of chromatogram quality across an isoeluotropic plane and a predicted chromatogram corresponding to a selected point on the isoeluotropic plane.

10 Claims, 6 Drawing Sheets

LIQUID CHROMATOGRAPHY

This is a continuation of application Ser. No. 07/513,351 filed Apr. 19, 1990, now abandoned.

BACKGROUND OF THE INVENTION

The invention relates to liquid chromatography apparatus and to a method of optimising solvent compositions for the analysis of a sample by liquid chromatography.

Chromatography has been used for many years to separate and measure the concentration of the constituents of complex mixtures. To analyze a sample in a liquid chromatograph apparatus an unknown sample is injected into a separating column together with a solvent (or mobile phase) or mixture of solvents. A detector at the far end of the column detects the presence of the constituents as they emerge or elute from the column. A chromatographer uses a plot of the detector output against time, known as a chromatogram, to analyze the unknown sample.

For example, an analyst may wish to know the concentration of a given pesticide in water or a given pharmaceutical drug in the bloodstream of a patient. In that case a known volume of the water or of the blood would be injected into a separating column and the constituent parts including the pesticide or the drug would be separately eluted and can be detected. By knowing when the particular constituents should elute their presence can be detected and quantative measurement may be made on the peaks.

Such a method of operation is very useful when the constituents of the sample are known. However, when the sample is an unknown, the chromatogram produced is more difficult to interpret. Further, research has shown that the separation of unknowns into their constituent parts in a liquid chromatograph is not always possible with a given multi-component solvent composition. As a result, analysts have varied the concentrations of the constituents of the solvent and have used solvents having up to four different major constituents enabling the separation of more kinds of unknowns into their component parts, provided a proper solvent composition can be selected. However, if an improper solvent composition is used, two or more components may co-elute, thereby producing a chromatogram with insufficient resolution. Thus chromatographers are left with the very time-consuming problem of randomly experimenting with the different solvent compositions and evaluating the chromatogram for each such experiment to determine which one is best. Typically, a chromatographer may perform a large number of experiments on a given unknown sample, each experiment being done with a different solvent composition in the column. A chromatogram is produced from each experiment. For a typical unknown, the chromatographer may perform many experiments before he discovers a set of conditions which are acceptable but, even so, perhaps not ideal for his purposes. Some of the chromatograms are easily discarded as being unusable but evaluating the remaining chromatograms to determine which is the most usable is very difficult. This task becomes even more difficult as the number of experiments increases as is required when three or four solvents are used in the column. Without a system and protocol it becomes highly unlikely that an optimum separation will be achieved by trial and error.

This problem has been addressed in a paper by Haleem J. Issaq entitled Computer-assisted HPLC which was published in American Laboratory, February 1983, pp 41–46. The paper describes a method based on statistical calculations whereby peak pair resolutions in 5 to 10 chromatographic runs using a combination of two or three pure or mixed solvents are plotted versus mobile phase composition. If no peak crossover takes place the resolution between each pair is used. If peak reversal does occur, the resolution between all peaks is calculated and used in determining the optimum mobile phase. The resulting overlapping resolution mapping (ORM) plots of each pair are then generated by the computer and indicate the regions where resolutions are above a level predetermined by the analyst. The union of all peak pair ORM plots, handled automatically by the computers, will give one plot indicating the region where all peak pair resolutions are above a predetermined level.

Since resolution versus mobile phase composition is used to generate the ORM plots, the analyst can program the computer to predict and print in the form of a table the peak pair resolutions for any desired mobile phase composition.

Retention times may be predicted if a plot of retention time, instead of resolution, is plotted versus mobile phase composition for each component in such mobile phase. This will be of value in showing how long it will take for the last component to elute from the column. In cases where resolution and not retention time is predicted, the analyst does not know how long the chromatographic run will take.

SUMMARY OF THE INVENTION

It is an object of the invention to enable provision of a method of and apparatus for aiding a chromatographer in optimizing solvent compositions for a given chromatographic separation.

The invention provides a method of optimizing solvent compositions for the analysis of a sample by liquid chromatography comprising the steps of:
a) selecting a plurality of solvent compositions,
b) performing a plurality of chromatographic analyses using each of the selected solvent compositions,
c) storing the chromatograms produced,
d) modelling the retention time of each peak with changing solvent composition,
e) modelling the quality of the chromatograms across a surface and producing and displaying the quality across the surface,
f) selecting a point on the surface,
g) displaying a predicted chromatogram corresponding to the selected point.

The invention allows the chromatographer to view a display representing the quality of the chromatograms and to select any point on the display and produce a predicted chromatogram using the solvent composition defined by that selected point. This provides a convenient way of testing the results produced by selecting a given solvent composition. Thus a chromatographer can quickly and simply select promising positions on the surface and have the predicted chromatogram simultaneously displayed.

The defined solvent compositions may lie on an isoeluotropic plane. This gives the advantage of a relatively constant separation line whichever solvent composition is selected for the sample measurement.

The quality of the modelled chromatograms may be displayed as a contour map. This enables easy selection of any point on the surface and provides an easily viewed representation of quality across the surface.

As an alternative to the display of the quality by a contour map it may be displayed as a response surface, that is a relief representation. Examples of such response surfaces are shown in a paper by P. J. Naish-Chamberlain and R. J. Lynch entitled "Evaluation of a Complete HPLC Solvent Optimisation System Involving Piece-Wise Quadratic Modelling" published in Chromatographia, Vol. 29, No. 1/2, January 1990, at pages 79-89. Such a representation, however, does not allow as easy a selection of points on the surface as a contour map due to the limitations of using a two-dimensional representation of a three dimensional surface.

The predicted chromatograph may be a line diagram showing the predicted peak positions. This gives a simple display producing a good indication of the quality of the chromatograph likely to be produced.

Various quality criteria may be used amongst which are: best overall separation of the peaks, best separation of a selected subset of the peaks, the time required for separation one(s) of all or a selected subset of the peaks.

Various other quality criteria could be mapped and used, for example any of those disclosed by P. J. Schoenmakers et al in Journal of Liquid Chromatography 10 (1987) pp 1865-1886; Chromatographia 24 (1987) pp 579-587; Journal of Chromatography 458 (1988) pp 358-370; or as disclosed by P. J. Schoenmakers in "Optimisation of Chromatic Selectivity" published by Elsevier, Amsterdam, 1986.

In step b) ten analyses may be performed. The number of analyses is chosen so as to obtain a sufficient precision of modelling without requiring an excessive number of analyses. Thus the greater the number of analyses the more precise it is possible to make the model but the longer it takes to carry out these analyses.

The peaks in each chromatogram may be identified and tracked by comparing their spectra with those of the peaks of a reference chromatogram. This is a convenient method of identification if a diode array detector is used. Other peak characteristics, for example area, time of elution, may be used either alternatively or additionally, singly or in combination to identify the peaks where these characteristics are available.

The invention further provides liquid chromatograph apparatus comprising:

a) a plurality of solvent sources;
b) solvent proportioning and pumping means;
c) a separating column;
d) sample input means;
e) a detector;
f) means for displaying a chromatogram;
g) control means for enabling the solvent composition for a given sample separation to be optimised, said control means comprising;
h) means for receiving and storing data representing the available solvents;
i) means for sequentially selecting solvent compositions using the available solvents and performing a chromatographic separation using the selected solvent composition;
j) means for storing each of the sequentially produced chromatograms;
k) means for detecting and labelling each of the peaks of each of the chromatograms;
l) means for predicting from the chromatograms stored the chromatographic peak positions over a surface;
m) means for displaying the chromatographic quality across the surface; and
n) means for selecting a desired point on the surface and displaying a predicted chromatogram simultaneously with the display of choromatographic quality.

Figure 1:
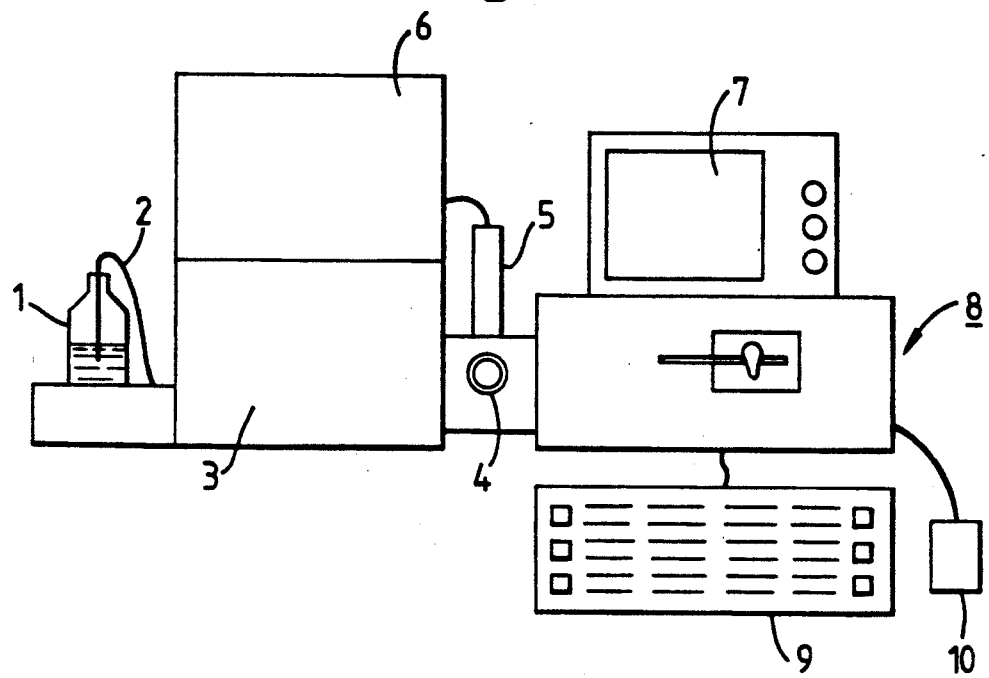
FIG. 1 shows in diagrammatic form a liquid chromatograph apparatus according to the invention.

DESCRIPTION OF THE PREFERRED
EMBODIMENTS

Embodiments of the invention will now be described by way of example with reference to the figures of the drawing.

FIG. 1 shows liquid chromatograph apparatus according to the invention and comprises a plurality of solvent sources one of which is shown as container 1 which is connected via a tube 2 to solvent proprotioning and pumping means 3 which may be formed for example by a Philips Scientific PU4100 pump. The outlet of the pump is connected via a sample injector 4 forming the sample input means to the inlet of a separating column 5. The outlet of the column 5 is connected to the input of a diode array detector 6 which may be that sold by Philips Scientific under the type number PU4120. The resulting chromatogram may be displayed on a VDU 7 or a hard copy may be obtained on a chart recorder or plotter (not shown). The control means for enabling the solvent composition for a given sample separation to be optimized is formed by a microcomputer 8 which includes a key board 9 and mouse 10 and may conveniently be formed by a Philips Scientific PU6003 diode array data system. It uses a plurality of chromatograms, for example ten, run under selected conditions and stored as data representing the chromatograms including peak shapes and peak spectra where a diode-array detector is used.

Optimization procedures can be classified as either sequential or interpretive. Sequential methods are typified by the commonly used Simplex procedure, with each set of chromatographic conditions being decided on the basis of a chromatographic response function from typically the previous three experiments. The problems with this approach include finding of a local optimum, rather than the global optimum, and the large number of experiments required, typically 25-30.

Interpretive methods involve the modelling of the retention times of the individual components, and consequently labelling of the peaks in each of the chromatograms used for modelling is necessary. An early example of the interpretive approach was the Sentinel system from Dupont, but this did not include peak labelling.

The software used in the control means uses an interpretive method and is built up of three distinct parts which perform the three functions of peak finding, peak labelling, and retention modelling and optimizing.

Figure 2:
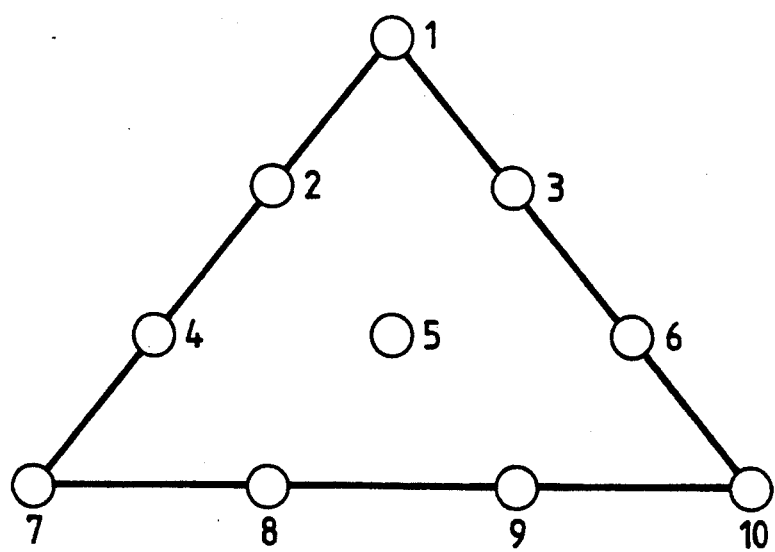
FIG. 2 shows ten points on an isoeluotropic triangle at which a chromatographic analysis is made in order to construct a rentention model.

Ten sets of data taken at points on an isoeluotropic triangle as shown in FIG. 2 are processed and the results used to predict the optimum chromatogram. The data for each point is loaded into memory, a chromatogram is selected as a reference chromatogram (usually a maxplot), and this is used to find the peak positions. The spectra are found for these peaks, conveniently by using a diode-array spectrometer as the detector, and are then used in peak labelling. The results of the labelling are saved in a chromatograms description file. This is a file which is progressively built up to contain the retention time and the peak size of all the peaks and is the raw data on which the model for the predicted optimum is based.

The overall process involves peak finding, peak labelling and retention modelling and optimizing. Peak finding is the process of finding the positions of resolved and partially resolved peaks, and the deconvolution of overlapping peaks. Peak finding can be achieved by firstly using the second derivative of each chromatogram, either at one wavelength or from a maxplot, which is the absorbance from the diode of highest absorbance at each individual time unit when using a diode array spectrometer as the detector. The three dimensional data are then broken down into segments containing the peaks and subsequently, for each segment, using a Principal Components Analysis (PCA) (singular value decomposition) to find the eigen-values. The principal components found are known as abstract chromatograms and spectra. These are used as inputs to an Iterative Target Transformation Factor Analysis (ITTFA) which uses the found peak positions as the starting points in a reconstruction of peak profiles. The individual spectrum for each peak is also reconstructed. This is done for each of the segments in all the chromatograms.

Further information on ITTFA can be obtained from the text book "Optimisation of Chromatographic Selectivity" by P. Schoenmakers, published by Elsevier, Amsterdam, 1986 and in a paper by B. G. M. Vandeginste, W. Derks and G. Kateman, starting at page 253 in Analytica Chimica Acta, 173 (1985).

The peaks are subsequently labelled against a reference set of spectra. Spectral and peak size information can be used for the matching. The spectral matching can be based on a least squares fit between the spectra. The reference set is established from ideally one chromatogram, the best-resolved chromatogram. If this is found subsequently not to contain the full set of components in the sample, the reference set can be updated, but then relabelling in all chromatograms will be required. The labelling in each chromatogram can be achieved by looking at the correlation between each of the reconstructed spectra and the reference spectra. Peak sizes or volumes may also be matched, and in addition the possibility of peaks containing more than one component may be taken into account in the overall assignment. This allows labelling of non-deconvoluted peaks. The best overall assignment is generally selected, but manual correction could be provided for. The labelled chromatograms are used as the inputs for the retention modelling. It should be noted that the peak reference spectra could alternatively be derived from more than one chromatogram if that enabled the individual peak spectra to be more easily determined.

The model employed requires an experimental design with 10 chromatographic runs of approximately equal retention time and consequently these data points should ideally lie on or close to an isoeluotropic plane. An acceptable range of retention-times, for example $k'=0.5-10$, is determined for one binary eluent, buffer/methanol for example in reverse-phase LC, (RPLC). The two other binary eluents, buffer/acetonitrile, and buffer/tetrahydrofuran in RPLC, can be defined, from factors relating the eluotropic strengths of these organic modifiers to those of methanol. These three corner points define an isoeluotropic plane. The simplest example is then to take a regular triangular design on this plane, (see FIG. 2). However, if there is more interest in one particular area, the design does not need to be regular.

For each component, corresponding to each reference compound, a mathematical model for retention is fitted to the ten points across the isoeluotropic plane. The numbering of the points is shown in FIG. 2. The model generates a retention surface which describes the movement of peaks with changing solvent compositions. These retention surfaces are the data used for calculating the selected response function(s), at all points across the plane. A selection of response functions can be generated, the choice being dependent on for example whether minimum time of analysis, or most even spacing of peaks is required. The response function can be tailored for all peaks or for a subset of peaks, such that if specific peaks are of interest and the rest are not, an optimum can be found specifically for the analytes of interest. Optima or other interesting points can be selected, and the chromatograms can be predicted at these positions. Comparisons can be made with collected data.

It should be noted that although the model used in this particular example requires approximately equal retention time this is not a necessary restriction of the invention. Models can be constructed which will allow for unequal retention times and under these circumstances the solvent compositions used may lie anywhere within or on the surface of the solvent tetrahedron (for a maximum of four solvents). For a two solvent mixture the points lie on an edge of the tetrahedron while for a three solvent mixture the points lie on a surface of the tetrahedron.

Figure 3:
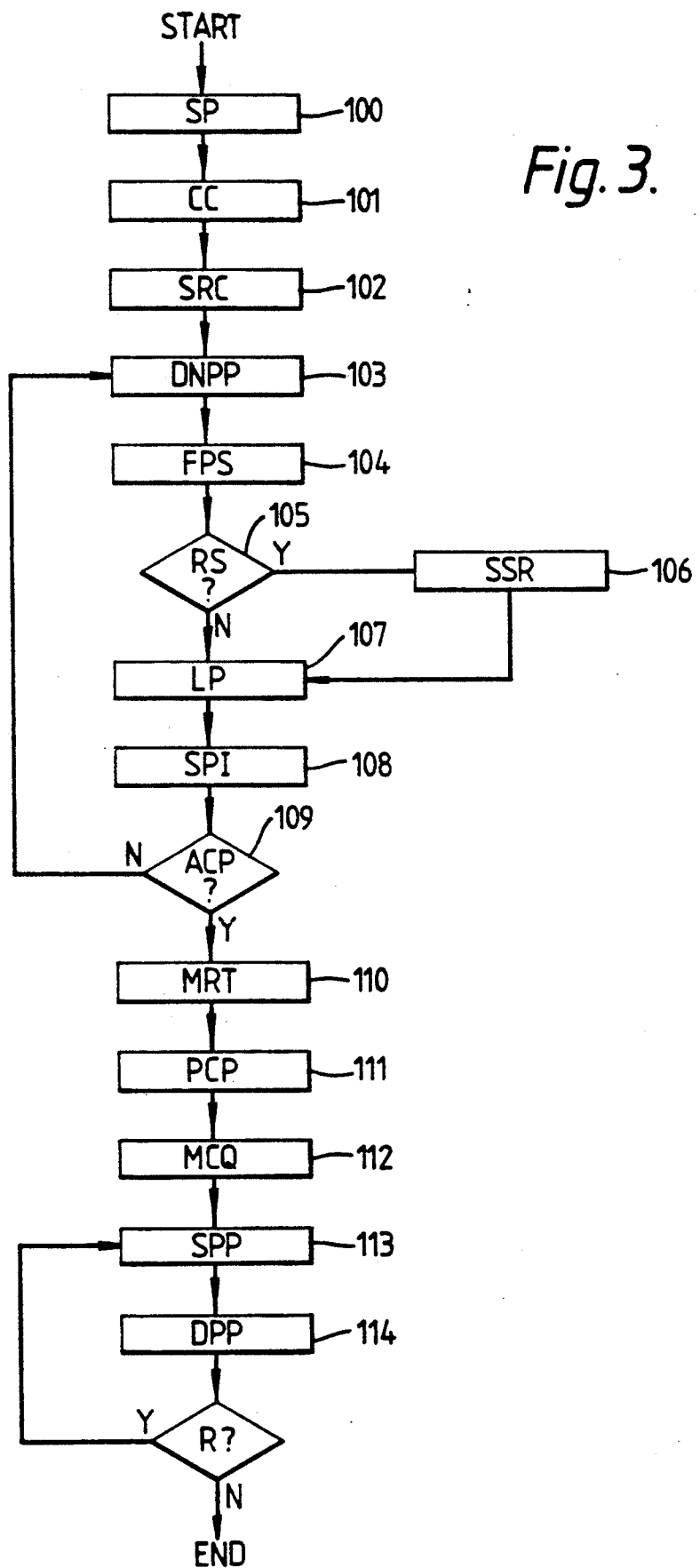
FIG. 3 is a flow diagram illustrating a method according to the invention of optimizing solvent compositions for the analysis of a sample by liquid chromatography.

FIG. 3 is a flow diagram illustrating a method according to the invention of optimizing the solvent composition for the analysis of a sample by liquid chromatography.

The first step of the method represented by box 100 labelled SP is to select the desired area for the search, for example the isoeluotropic triangle shown in FIG. 2. This selection is made by the chromatographer using known criteria and for further details of how to make the choice reference should be made to the book by P. Schoenmakers referenced hereinbefore. The next step represented by Box 101 labelled CC is to run analyses at each of the ten points on the isoeluotropic triangle shown in FIG. 2 and to collect the resulting chromatograms. It should be noted that, although ten points are shown in FIG. 2, it is not essential to the method that ten points are used. A greater number of points will enable a more precise modelling to be carried out at the expense of a greater number of experiments being needed while a lesser number of points will require fewer experiments but will also result in a less precise modelling. This may be achieved by collecting hard copies from a chart recorder or plotter or they may be read directly into memory and displayed on the VDU 7. The chromatograper then selects the reference chromatogram, represented on the flow chart by Box 102 labelled SRC. This will normally be the chromatogram having the largest number of clearly resolved peaks. The next step represented by Box 103 labelled DNPP is to determine the number and position of the peaks of the chromatogram. This can be done by a variety of methods which may for example involve mathematical deconvolution to resolve overlapping peaks or the production of the second derivative of the chromatogram to locate the positions of the peaks. Once the number and positions of the peaks have been determined, the spectra of the peaks are obtained as represented by Box 104 labelled FPS. Since a diode-array spectrometer is used as the detector and a complete spectrum is measured and stored at regular intervals, for example once per second, the spectral characteristics of each peak can be determined. The spectra may be refined by the ITTFA process.

When the position and number of peaks of the chromatogram and their spectra have been found then it is determined whether the chromatogram being considered is the reference chromatogram Box 105 labelled RS?. If this is the case, then the spectra are stored as the reference, Box 106 labelled SSR. If the chromatogram is not the reference chromatogram then the peaks of the chromatogram are identified, Box 107 labelled LP, by comparing the spectrum of each peak with those of the peaks of the reference chromatogram, it being assumed that if the spectra correlate then the peaks are of the same constituents. If two or more peaks have similar spectra making it difficult to identify individual peaks with certainty, other peak characteristics may also be compared, for example "peak volume" i.e. area under the spectrum x elution profile. When the peaks have been identified each is stored with its retention time and the solvent composition, Box 108 labelled SPI.

Figure 4:
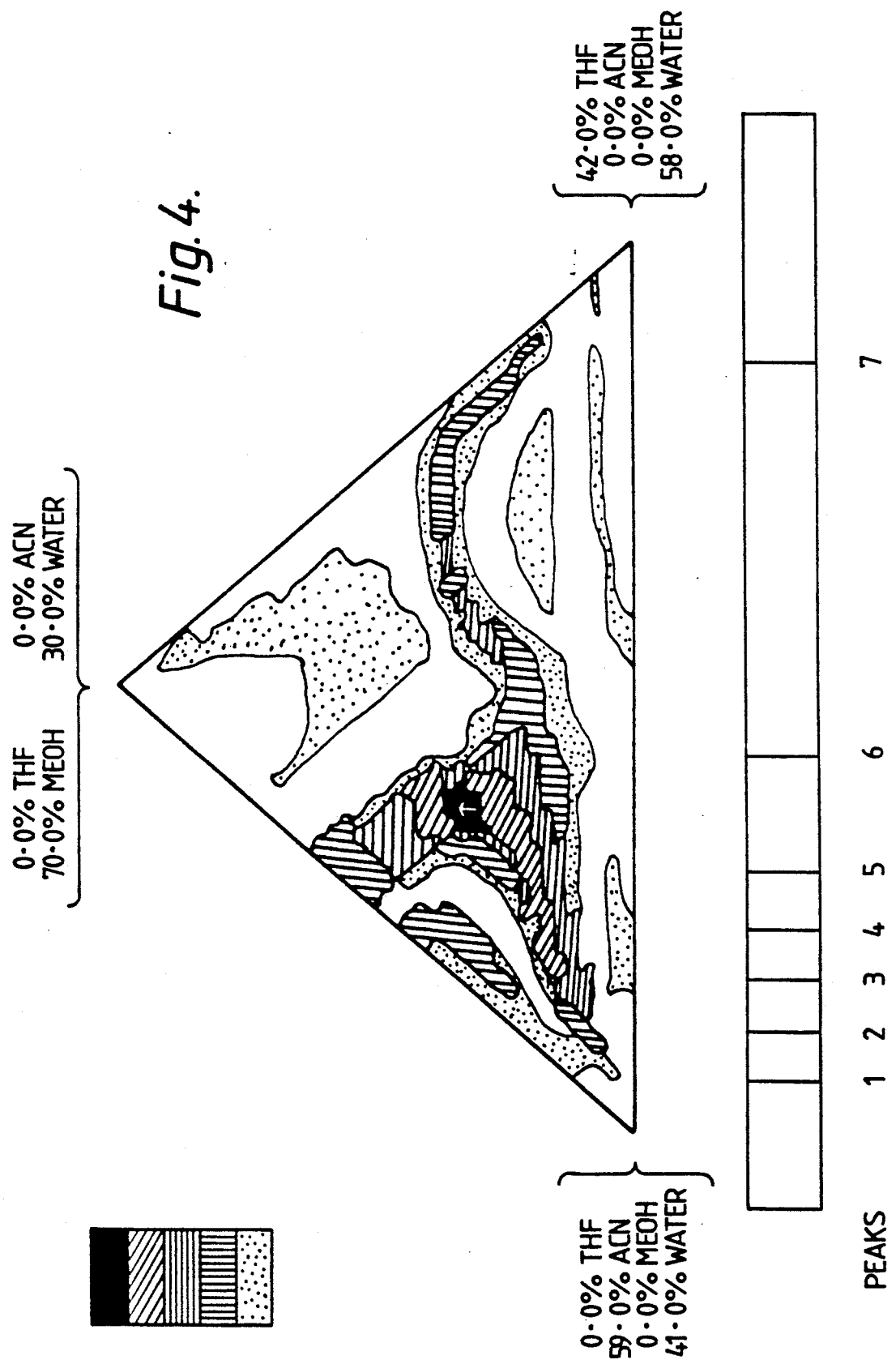
FIGS. 4 to 7 show displays of contour maps and diagrammatic chromatograms which are displayed simultaneously on the display unit of the microcomputer forming part of the chromatograph apparatus of FIG. 1.
Figure 5:
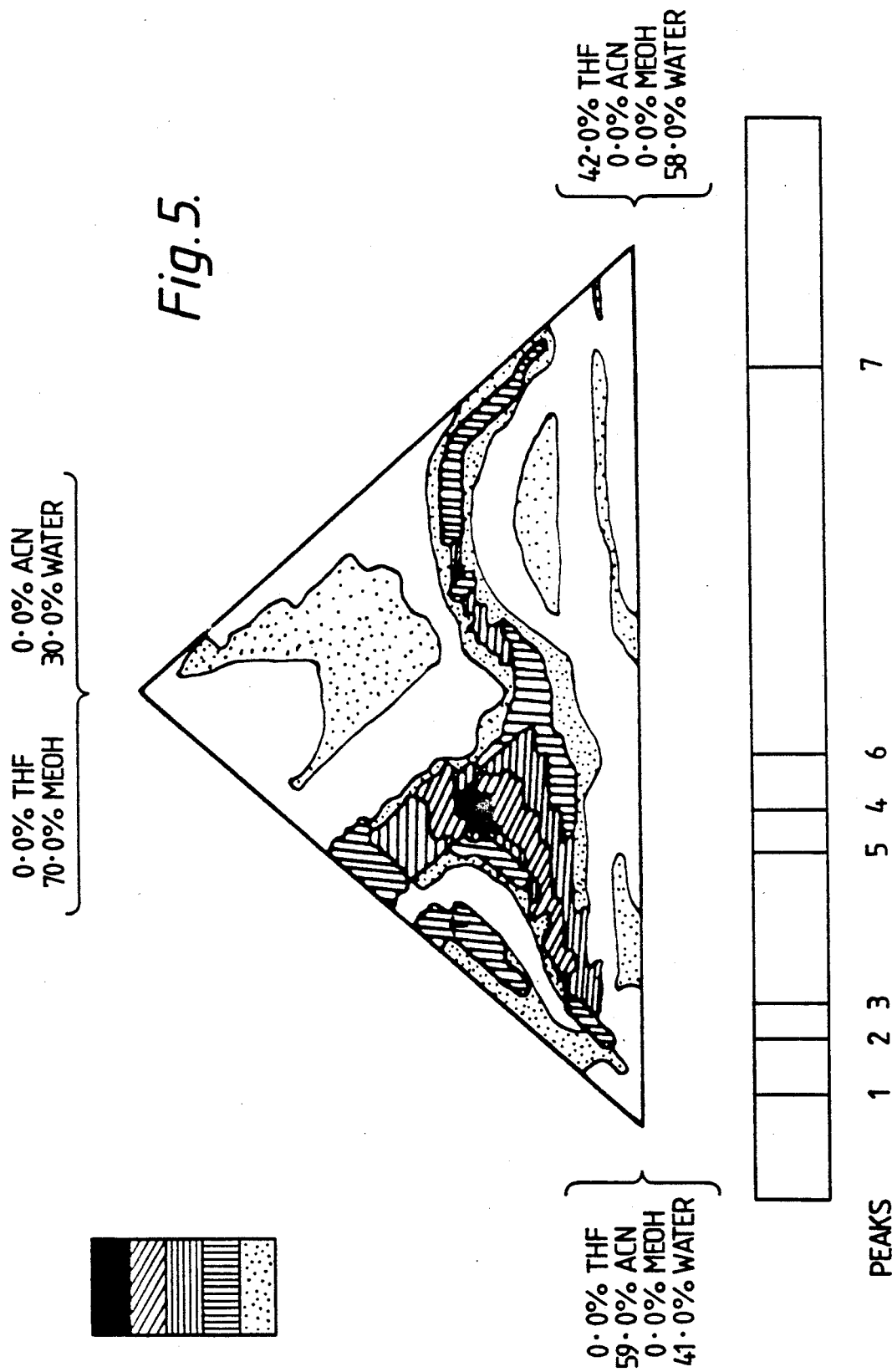
Figure 6:
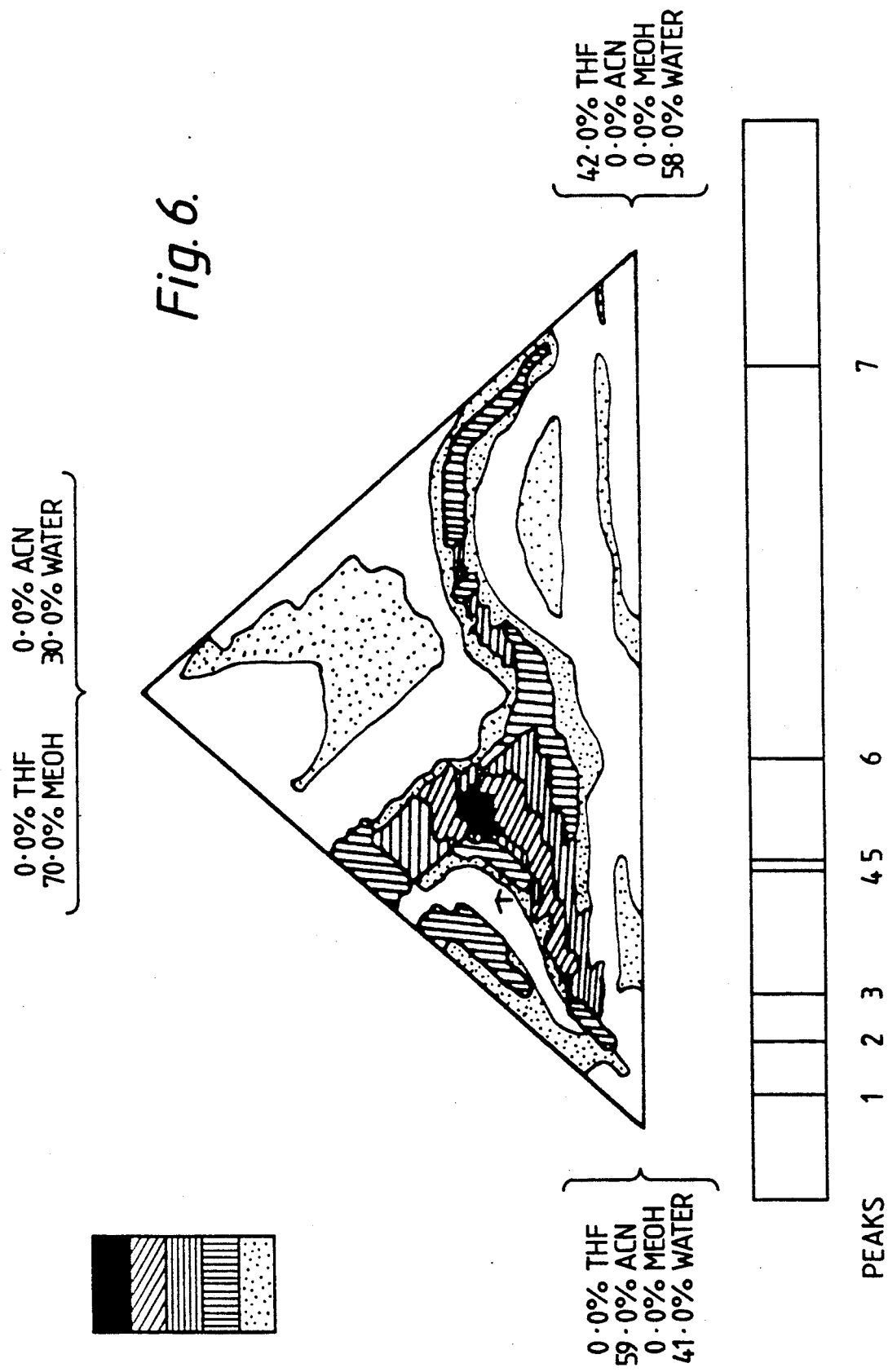

If further chromatograms are to be processed then the procedure reverts to Box 103 as shown by decision process 109 labelled ACP?. If all the chromatograms have been processed then the retention time for each peak is modelled across the isoeluotropic triangle, Box 110 labelled MRT. The next step, Box 111 labelled PCP, is to predict the chromatograms across the isoeluotropic triangle. The chromatogram quality is then modelled across the isoeluotropic triangle and is displayed in the form of contours on the surface of the triangle. This process is represented by Box 112 labelled MCQ. Various criteria may be used to assess quality, for example one or more of the resolution values of pairs of successive peaks, the time required for separation, the lowest resolution value occurring in the chromatogram, or any of those disclosed in the publications of P. J. Schoenmakers et al referred to herein. FIGS. 4 to 7 show examples of the resulting displays of the quality contours on the isoeluotropic triangle. FIGS. 4 to 6 show the case where the quality criterion is the maximum overall resolution of the peaks while in FIG. 7 the quality criterion is the maximum resolution of peak 6 regardless of the resolution of pairs of insignificant peaks.

The chromatographer now has a visual indication of the quality, according to the selected criteria, of a separation displayed on the VDU 7. It is now possible to select a point on the triangle, for example by means of the mouse 10 and a cursor on the display. When this point is selected, as represented by Box 113 labelled SPP, a line diagram of the position of the chromatogram peaks corresponding to an analysis using the selected solvent composition is produced on the display concurrently with the contour map on the triangle, Box 114 labelled DPP. If the chromatographer is not satisfied for any reason with the predicted chromatogram for the selected solvent composition the process can be repeated, as indicated by Box 115 labelled R?, and a new predicted chromatogram displayed. While in this particular embodiment only the peak positions are displayed, it would be possible to display a predicted chromatogram showing peak heights and separations to give the chromatographer further assistance.

Figure 7:
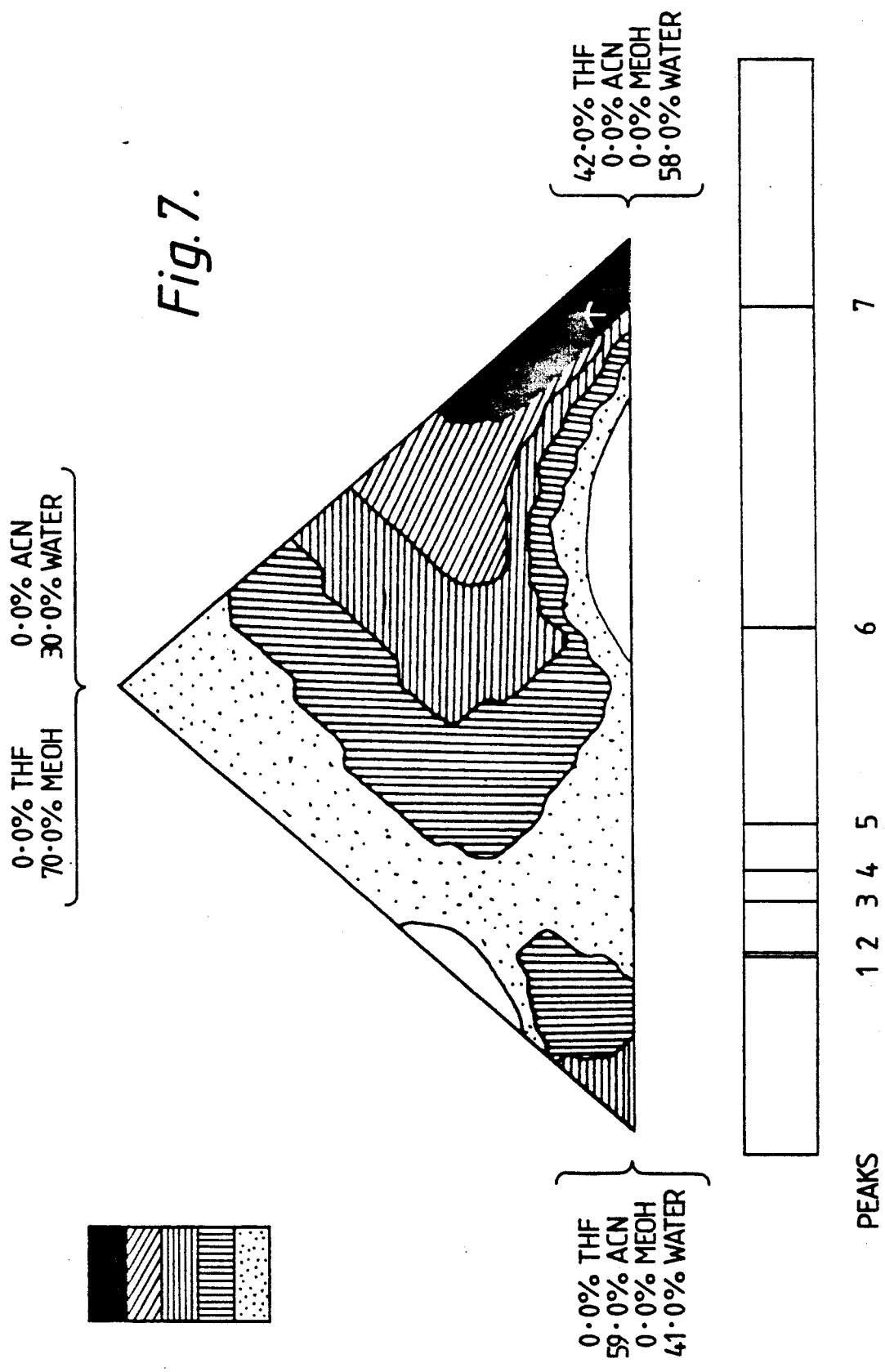

FIG. 4 shows the predicted chromatogram when a point (MEOH-22.7%, ACN-28.0%, THF8.4%) within the highest quality contour is selected and it can be seen that an optimum separation has been achieved. FIG. 5 shows the predicted chromatogram when a point (MEOH-24.1%, ACN-36.5%, THF 1.6%) within a local maximum is selected as opposed to FIG. 4 in which the global maximum was selected. In this case it can be seen that the peaks are reasonably separated though not as optimally as in FIG. 4 but it should also be noted that peaks 4 and 5 have changed order of elution. Thus the feature of labelling the peaks using spectra from the diode array has proved its usefulness. However, if a diode array detector is not available the peak identification may be carried out using other peak characteristics. FIG. 6 shows the predicted chromatogram when a point (MEOH-21.4%, ACN-34.5%, THF-4/6%) is selected where a low quality is expected according to the criteria under which the contour map was constructed. However, it can be seen that this particular solvent composition would be satisfactory if the chromatographer was not interested in peaks 4 and 5. FIG. 7 shows the contour map constructed according to the criterion that peak 6 should have the maximum resolution. As can be see from the predicted chromatogram displayed corresponding to a selected point (MEOH-7.0%, ACN-1.5%, THF-36.7%) peak 6 is well separated for the selected solvent composition but peaks 1 and 2, for example, are not.

While the predicted chromatograms shown in FIGS. 4 to 7 are in the form of line diagrams it is possible using the ITTFA process to construct a true predicted chromatogram giving the peak profiles. This has the advantage of giving a more comprehensive display to the chromatographer allowing better choice of solvent composition, for example if sharp peaks are predicted their separation may be smaller than that of broader peaks to give the same resolution. It does, however, require more processing of the data in order to produce the predictions of the peak profiles. Further it is possible to display simultaneously a plurality of predicted chromatograms corresponding to a plurality of selected points on the contour map. The chromatograms may conveniently be displayed one above the other on the display above, below, or to one side of the contour map. Clearly the particular arrangement of the predicted chromatogram(s) and the contour map is a matter of choosing the most convenient arrangement and the arrangement shown in FIGS. 4 to 7 is only one among many possibilities.

It is also possible to label the peaks by the chemical compounds they contain in certain circumstances.

These compounds can be identified for example from their characteristic UV Spectrum, from comparing the time taken for the peak to elute from the column as compared with a sample of the pure compound or by any other technique which analysts use to identify the peak compound. This can be done when the starting materials for example of a pharmaceutical substance are known. An intermediate state where some peaks are assigned numbers and some labelled with the known compound is also possible. The labels may be displayed adjacent to the relevant peaks on the displayed chromatogram or as a separate table i.e. the peaks are numbered and the corresponding compounds listed in a separately displayed table against the respective numbers.

From reading the present disclosure, other modifications will be apparent to persons skilled in the art and which may be used instead of liquid chromatograph apparatus and component parts thereof and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalization of one or more of those features which would be obvious to persons skilled in the art, whether or not it relates to the same invention as presently claimed in any claim and whether or not it mitigates any or all of the same technical problems as does the present invention.

We claim:

1. A method of optimizing solvent compositions for the analysis of a sample by liquid chromatography comprising the steps of:
    (a) defining a plurality of solvent compositions,
    (b) performing a plurality of chromatographic analyses using the defined solvent compositions,
    (c) storing the chromatograms produced,
    (d) labeling each peak in each of said chromatograms
    (e) modelling the retention time of each peak with changing solvent composition,
    (f) modelling a quality of the chromatograms across a surface and producing and displaying the quality across the surface,
    (g) selecting a point on the surface,
    (h) displaying a predicted chromatogram corresponding to the selected point.

2. A method as claimed in claim 1, in which the defined solvents lie on an isoeluotropic plane.

3. A method as claimed in claim 1 in which the quality of the modelled chromatograms is displayed as a contour map.

4. A method as claimed in claim 1, in which the predicted chromatogram is a line diagram showing the predicted peak positions.

5. A method as claimed in claim 1, in which the quality criterion is the best overall separation of the peaks.

6. A method as claimed in claim 1, in which the quality criterion is the best separation of a selected subset of the peak(s).

7. A method as claimed in any of claims 1 to 4, in which the quality criterion is the time taken for the selected peak(s) to be separated.

8. A method as claimed in claim 1 in which in step b) ten analyses are performed.

9. A method as claimed in claim 1 in which the peaks in each chromatogram are identified and tracked by comparing their spectra with those of a set of reference peaks.

10. A method as claimed in claim 9 in which the reference peaks are derived from one or more of the plurality of the chromatograms stored in accordance with step c.

* * * * *